(12) United States Patent
Nooshin

(10) Patent No.: US 8,011,693 B2
(45) Date of Patent: Sep. 6, 2011

(54) THERMOREGULATORY UNIT FOR SMALL HUMAN TRANSPORT SYSTEM

(75) Inventor: Seyed Ali Reza Nooshin, Toronto (CA)

(73) Assignees: Seyed Ali Reza Nooshin, Newmarket, Ontario (CA); Seyedeh Delaram Zehedi, Newmarket, Ontario (CA)

( * ) Notice: Subject to any disclaimer, the term of this patent is extended or adjusted under 35 U.S.C. 154(b) by 231 days.

(21) Appl. No.: 12/398,198

(22) Filed: Mar. 5, 2009

(65) Prior Publication Data

US 2009/0261137 A1    Oct. 22, 2009

(51) Int. Cl.
*B60R 99/00* (2009.01)

(52) U.S. Cl. .................. 280/762; 280/47.34; 280/304.1; 280/647; 280/650

(58) Field of Classification Search ............... 280/47.38, 280/304.1, 647, 650, 658, 251
See application file for complete search history.

(56) References Cited

U.S. PATENT DOCUMENTS

| | | | | |
|---|---|---|---|---|
| 3,850,006 A * | 11/1974 | Redfern et al. | ................ | 62/216 |
| 5,943,716 A * | 8/1999 | Chu | .................................. | 5/423 |
| 6,027,137 A * | 2/2000 | Rura | ............................ | 280/650 |
| 6,170,282 B1 * | 1/2001 | Eddins | ........................ | 62/259.3 |
| 6,217,099 B1 * | 4/2001 | McKinney et al. | .......... | 296/77.1 |
| 6,979,018 B2 * | 12/2005 | Kassai et al. | ................. | 280/648 |
| 2007/0018415 A1 * | 1/2007 | Koch | ........................ | 280/47.38 |
| 2007/0080519 A1 * | 4/2007 | Murdock | ..................... | 280/650 |
| 2008/0084040 A1 * | 4/2008 | McGowan | ................ | 280/47.38 |

* cited by examiner

*Primary Examiner* — Hau Phan
*Assistant Examiner* — Bryan Evans

(57) ABSTRACT

The designed invention relates to a temperature regulation device for both hot and cold climates primarily for occupants of human transport mediums such as strollers, wheelchairs, and scooters and secondarily for the caregivers who use these mobile mediums. The invention comprises of an enclosed compartment to hold the occupant, and at least one thermoregulatory unit, comprising at least one thermoelectric element, connected to the compartment.

10 Claims, 6 Drawing Sheets

11

THERMOREGULATORY UNIT FOR SMALL HUMAN TRANSPORT SYSTEM

CROSS REFERENCE TO RELATED APPLICATION

This application claims the benefit of the earlier filed Canadian patent application, with application number 2624237, file on Mar. 6, 2008, the entire contents of which are herein incorporated by reference.

FIELD OF INVENTION

The designed invention relates to temperature regulation for both the occupants of human transport mediums such as strollers, wheelchairs, and scooters as well as the caregivers who use these mobile mediums.

BACKGROUND

Wheelchairs, scooters and the like are commonly used to provide mobility for disabled individuals. Strollers and baby carriages are used by parents to transport young children. While the added mobility is beneficial, difficulties remain. For example, during hot summers and cold winters, these units do not provide any protection against extremes of temperatures. Vehicles have air conditioners and heaters to provide comfort for the passengers in these otherwise uncomfortable surroundings. Therefore, there has been a neglected group in the art for occupant compartments of strollers, wheelchairs, and scooters. These groups now have an improvement that can bring the comfort and warmth of both cooling and heating into the compartment of these transport mediums.

DESCRIPTION OF THE RELATED ART

WIPO patent no. WO 00/48546 relates to a method of heating and cooling infant incubator chambers during transport with the use of thermoelectric devices and an external power supply.

The prior art shows the concept of using thermoelectric devices for heating/cooling applications for a compartment, but the problem is that the design would not be practical for use in strollers, wheelchairs, and scooters because their design has air flow for the inside heat exchanger in a perpendicular direction to the air flow of the exhaust heat exchanger. Such a design would be inefficient in stroller applications due to size and orientation. In addition, the design lacks adjustable and flexible tubes to efficiently manage and direct air within the enclosure.

WIPO patent application no. WO 2007/108810 relates to using thermoelectric devices for heating and cooling strollers, cribs, and wheelchairs. The problem with the prior art is that the design lacks the principle use of air recirculation to increase unit efficiency. Furthermore, for mobile application, the device is required to be placed behind the seat which can affect the stability and safety of strollers by moving the centre of gravity towards the back. In addition, the design places the undesired exhaust air directly in front of the caregiver thereby causing the caregiver's body temperature to rise more in hot environments and to fall more in cold environments.

SUMMARY OF THE INVENTION

This invention is designed to overcome the shortcomings of prior art in the field of human transport mediums such as strollers, wheelchairs, and scooters.

An apparatus in accord with the invention, comprised of an enclosed occupant compartment to hold the occupant, and at least one thermoregulatory unit, comprising of at least one thermoelectric element, connected to the compartment in an air re-circulation method, capable of both cooling and heating the air in the compartment.

In one embodiment, the apparatus in accord with the invention has a plurality of flexible, movable, and adjustable air tubes.

In another embodiment, the apparatus in accord with the invention has adjustable tubes that allow desired air to go to both the compartment and the caregiver.

The apparatus in accord with the invention has an occupant compartment which can either be a stroller, wheelchair, or scooter.

In another construction, the apparatus in accord with the invention has an enclosed compartment to hold the occupant, one thermoregulatory unit, comprising one thermoelectric element, connected to the compartment, able to both cool and heat the air in the compartment, where the compartment has a plurality of flexible air tubes, where the thermoregulatory unit includes at least one fan, where the thermoregulatory unit is removably attached behind a seat of a stroller, wheelchair, or scooter and where the thermoregulatory unit is powered by batteries.

In another application, the apparatus in accord with the invention is able to keep occupants in a temperature controlled environment by enclosing the compartment with a rain guard with shade guard so that a significant amount of compartment is sheltered from the external environment and the sun; then starting the thermoregulatory unit, which is able to regulate the temperature within the compartment.

An advantage of the invention is that the same apparatus can be used to cool and warm both the occupants inside a compartment and the caregiver at the same time.

Another advantage of the invention is that it can be equipped with air filters to reduce the amount of harmful airborne materials that might enter the compartment.

Another advantage of the invention is that the flexible tubes allow the apparatus in accord with the invention to be placed in various locations and to direct the air to exactly the locations that are desired by the user.

Another advantage of the invention is that the apparatus of the invention can add stability to the human transport medium by placing the invention underneath the stroller seat.

Another advantage of the invention is that the exhaust air outlet is set so that the unwanted exhaust air is never in the line of the caregiver.

The foregoing, and other features and advantages of the invention, will be apparent from the following, more particular description of the preferred embodiments of the invention, the accompanying drawings, and the claims.

BRIEF DESCRIPTION OF THE DRAWINGS

FIG. 5 is a perspective of the first (stroller) embodiment of the invention with a rain guard on.

DRAWINGS

Reference Numerals

Figure 1:
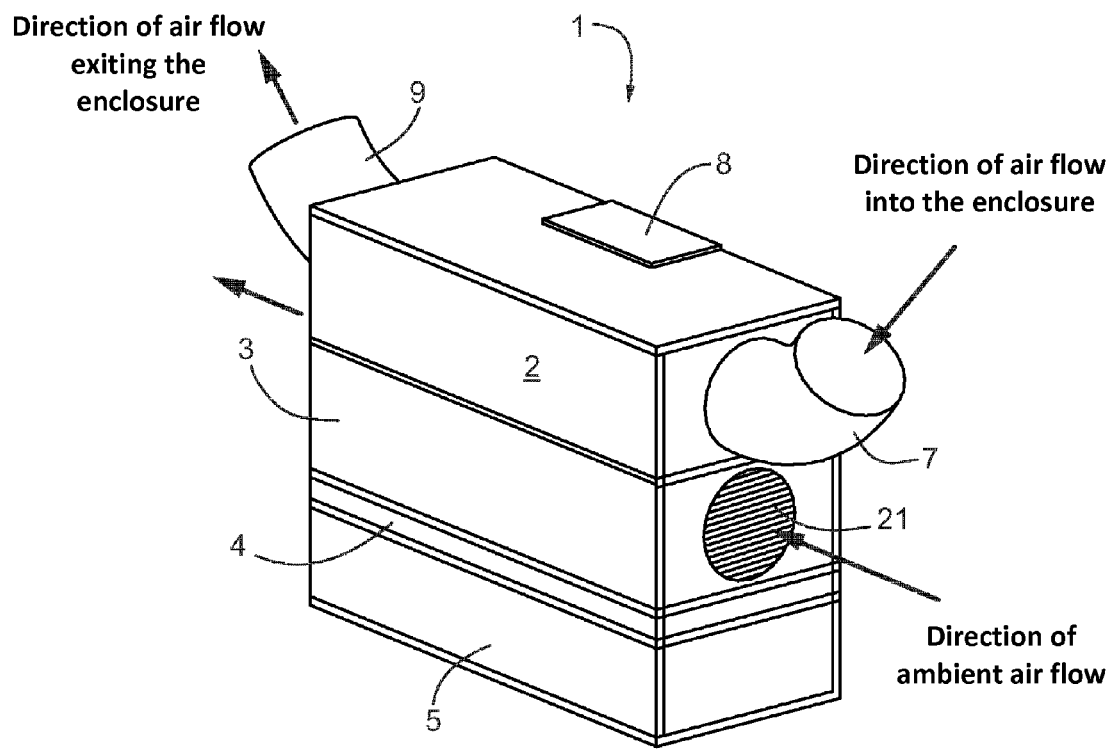
FIG. 1 is the isometric front view of the thermoregulatory unit.
Figure 2:
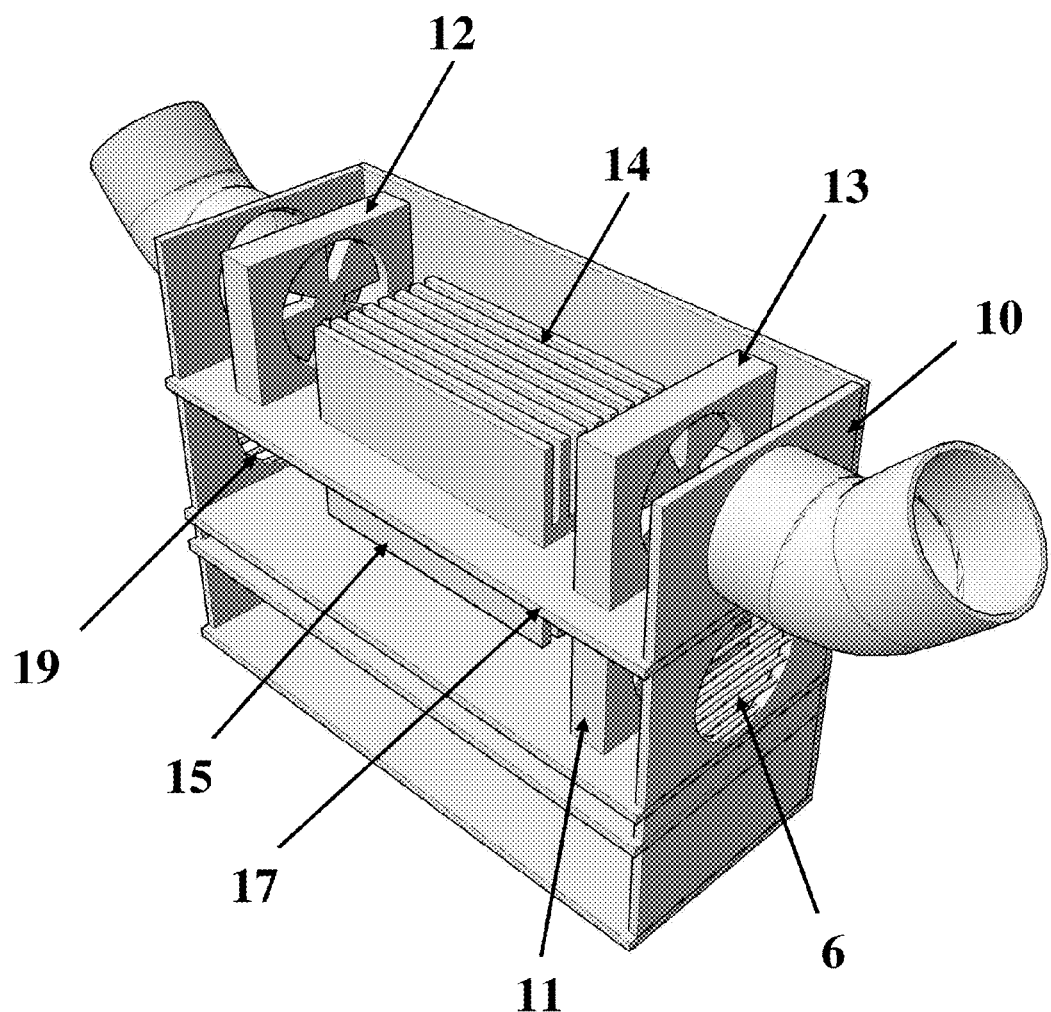
FIG. 2 is the isometric front view of the thermoregulatory unit without the front and top cover.
Figure 3:
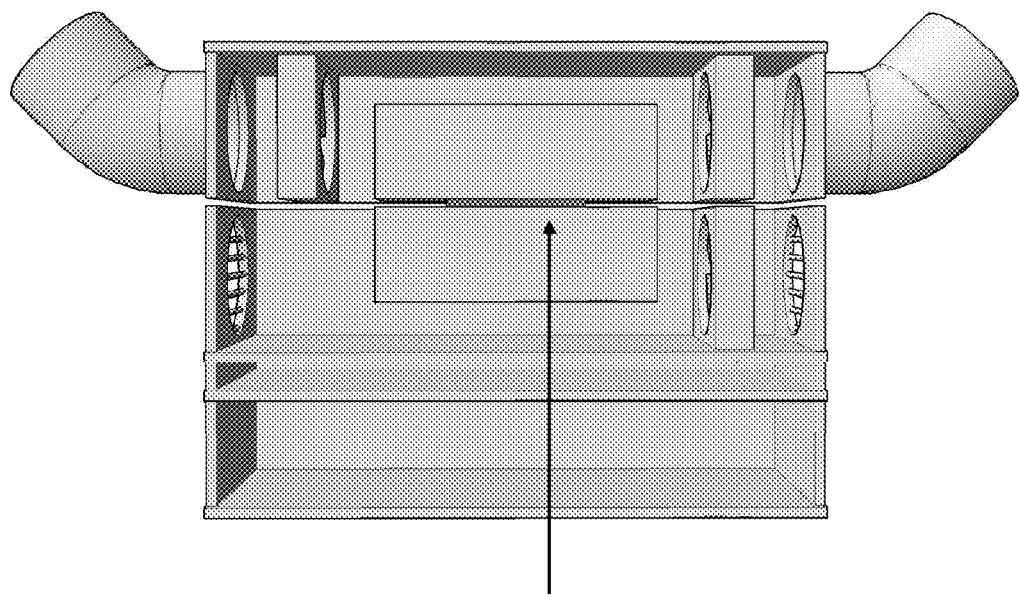
FIG. 3 is the front view of the thermoregulatory unit with the side wall and insulating divider removed to reveal the thermoelectric device within.
Figure 4:
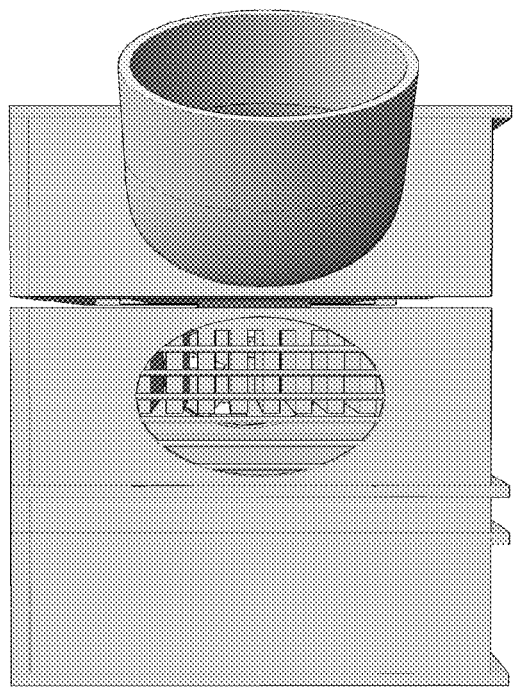
FIG. 4 is the side view of the thermoregulatory unit with the insulating divider removed.

1 Thermoregulatory unit
2 Active Chamber
3 Exhaust Chamber
4 Electronics Chamber
5 Battery compartment
6 Inlet exhaust air
7 Outlet air to enclosure
8 Control panel
9 Inlet air from enclosure
10 Fresh air opening side panel
11 Inlet exhaust fan
12 Inlet fan from enclosure
13 Outlet fan to enclosure
14 Heat exchanger in Active Chamber
15 Heat exchanger in Exhaust Chamber
16 Thermoelectric unit (TE)
17 Insulating divider
18 Rain cover
19 Outlet exhaust air to environment

DETAILED DESCRIPTION OF THE DRAWINGS

In the following detailed description of various embodiments of the invention, numerous specific details are set forth in order to provide a through understanding of various aspects of one or more embodiments of the invention, however, one or more embodiments of the invention may be practiced without these specific details. In other instances, well-known methods, procedures, and/or components have not been described in detail so as not to unnecessarily obscure aspects of embodiments of the invention.

This invention is generally directed to compartments that allow the temperature in the occupant's environment to be regulated. The following description is directed towards, but not limited to, three possible embodiments of the invention, namely, the stroller, wheelchair, and scooter.

DEFINITIONS

Compartment: herein defined as a confined, predetermined area that allows the occupant, whether a baby, child or an adult, to sit, stand, or lie down; which can be either stationary or mobile, and includes walker strollers, jogger strollers, wheelchairs, and scooters.
Occupant(s): adult, child, infant, or baby.
Stroller: a mobile occupant's scooter, including walkers, joggers, scooters, and wheel chairs, in which an occupant may be placed.
Rain guard or cover: a plastic or canvas type material, part of which is transparent, that is conventionally used to cover strollers so that the occupant is secluded from the external environment.
Caregiver: person caring for occupant.
Information: text, still images, moving images, sounds, vibrations, or any combination thereof.
Active chamber: chamber where heat transfer takes place to create the desired air that will be entering the enclosure.
Exhaust chamber: chamber where heat transfer takes place and the undesired air is expelled back into the environment.

FIG. 1-4 shows the thermoregulatory unit 1 that will be used in all embodiments of the invention disclosed herein. The thermoregulatory unit is comprised of two heat exchangers 14 and 15; an outlet exhaust fan 11; an inlet fan from enclosure 12; an outlet fan to enclosure 13; a thermoelectric element (TE) 16; insulating divider 17; an Active Chamber 2; an Exhaust Chamber 3; an Electronics Chamber 4 and a battery compartment 5.

TE device is the primary method of transferring heat between the active chamber 2 and the exhaust chamber 3. The TE device is based on the principles of the thermoelectric effect (also known as the Peltier effect) which states that when an electric current is applied to two dissimilar materials, the TE device acts like a heat pump that transfers heat from one side of the device to the other side against the temperature gradient. The direction of the heat transfer depends on the polarity of the current applied. Therefore, to switch between cooling to heating and vice versa, a change in direction of the current will achieve this result. It should be noted that TE devices are used extensively in small cooling applications since they are able to maintain temperatures to within 0.1 degrees Celsius. Additional thermoelectric elements may be stacked to achieve even lower temperatures.

When the device has been turned on and set to air conditioning mode, initially air within the enclosed compartment (assumed ambient temperature) will be sucked in through an inlet tube 9 that is placed within the enclosed compartment that will direct the air into the active chamber of the unit 2. The inlet air to the device is forced in through the inlet pipe with the aid of a forced air circulating unit such as a fan 12. The active chamber 2 is where the inlet air from the enclosed compartment will either get cooled down (if in Air conditioning mode) or heated up (if in Heating mode). Once the air enters the active chamber 2, the air will be directed and forced towards a heat exchanger 14 with an air circulating device such as a fan 12. Once the inlet air has been forced towards the heat exchanger within the active chamber, the heat exchanger 14 will absorb the heat from the air being blown over causing the overall temperature of the air to drop. The cooled air (now below ambient) will then be forced towards another air circulating device 13 that will push the colder air out of the outlet tube 7 and back to the enclosed compartment. This cycle then repeats itself to gradually reduce/increase the temperature of the user compartment depending on the mode that the device has been set to.

The heat that was absorbed by the heat exchanger in the active chamber 2 will transfer to the Thermo-Electric (TE) device(s) 16 through the heat exchanger in the Active Chamber 14. In Air conditioning mode, the TE device 16 will have the cold side in direct contact with the active chamber's heat exchanger. By being in direct contact, the heat absorbed from the heat exchanger 14 will be transferred to the surface of the cold side of the TE device. Heat is pushed from the cold side of the TE device to the hot side of the TE device through the use of the unique property of Thermo-electric devices and the current that flows through the TE device. Once the heat has been transferred to the hot side, there is a heat exchanger in direct contact with the hot side of the TE device that will transfer the heat from the hot side to the heat exchanger 15 which is located in the exhaust chamber 3. The exhaust chamber will always have the opposite mode of the active chamber (eg. If the active chamber is cooling the air, the exhaust chamber will be expelling hot air). Once the heat from the hot side of the TE has been transferred to the exhaust chamber's heat exchanger 15, this heat is released to the forced air that flows over and through the exhaust chamber's heat exchanger 15. The inlet fan device within the exhaust chamber is used to bring ambient air into the exhaust chamber and to expel the heated air back into the atmosphere through the exhaust chamber outlet 20. It is understood that a small cover can be placed at the exhaust chamber 3 so that the expelled air does not come into contact with air coming back from the enclosure 9. The power source that is used to run the air circulating unit, TE device, and any other electric components are heavy duty rechargeable batteries (other methods of power are possible). This cycle then repeats itself to gradually reduce/increase the temperature of the user compartment depending on the mode that the device has been set to.

It should be noted that the TE device 16 should be (but not limited to) enclosed within the floor that separates the active chamber and the exhaust chamber to provide good insulation and efficient heat transfer between the hot and cold side of the TE device.

It should also be noted that if the device is set to heating mode, the same principles apply with the only changes being that the active chamber 2 will be hot and will heat the air within this chamber and that the hot side of the TE device 16 will be towards the active chamber and the cold side of the TE device 16 will be towards the heat exchanger in the exhaust chamber 3 where the expelled outlet air from the exhaust chamber will be colder since it will be cooled by the heat exchanger in the exhaust chamber.

The thermoregulatory unit 1 is controlled by a movable and adjustable control panel box 8. The control panel may also provide for indicating variables, but not limited to, internal and external temperature, mode, and settings, as well as a switch for the user to input their own desired temperature. It should also be noted that the buttons of the control panel can come in many different forms. The simplest form of the control panel 8 would be one 3 way switch that can be set to HEAT, COOL, OFF with constant current and fan speed gong through the thermoregulatory unit 1.

It should also be noted that the compartment does not have to be enclosed but an enclosed compartment does greatly increase the efficiency of the device. As the amount of air gaps decrease, the efficiency of the device increases so this should be taken into consideration by the users of the device.

Figure 5:
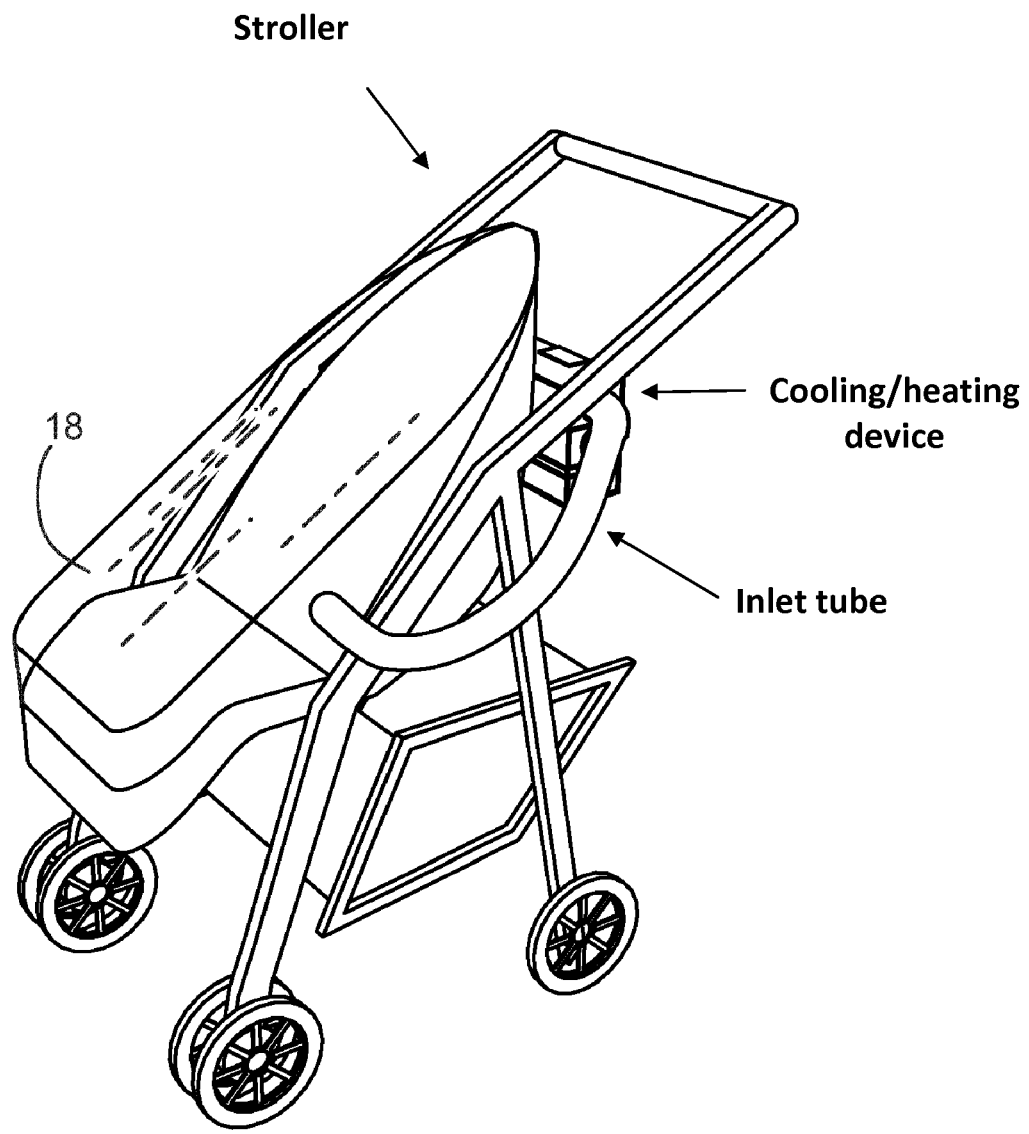

FIG. 5 is an illustration of a stroller and the implementation of the embodiment of the invention with the thermoregulatory unit 1 positioned at the back of the stroller close to the caregiver. In the preferred embodiment, all tubes are insulated on the outside and have smooth inner walls. The rain cover 18 will be the tool used to shelter the occupant from external environment and retain any heating/cooling benefits provided by the invention. It will be understood that wheel chairs, because of their similarities with strollers, can be similarly equipped with the thermoregulatory unit 1.

Figure 6:
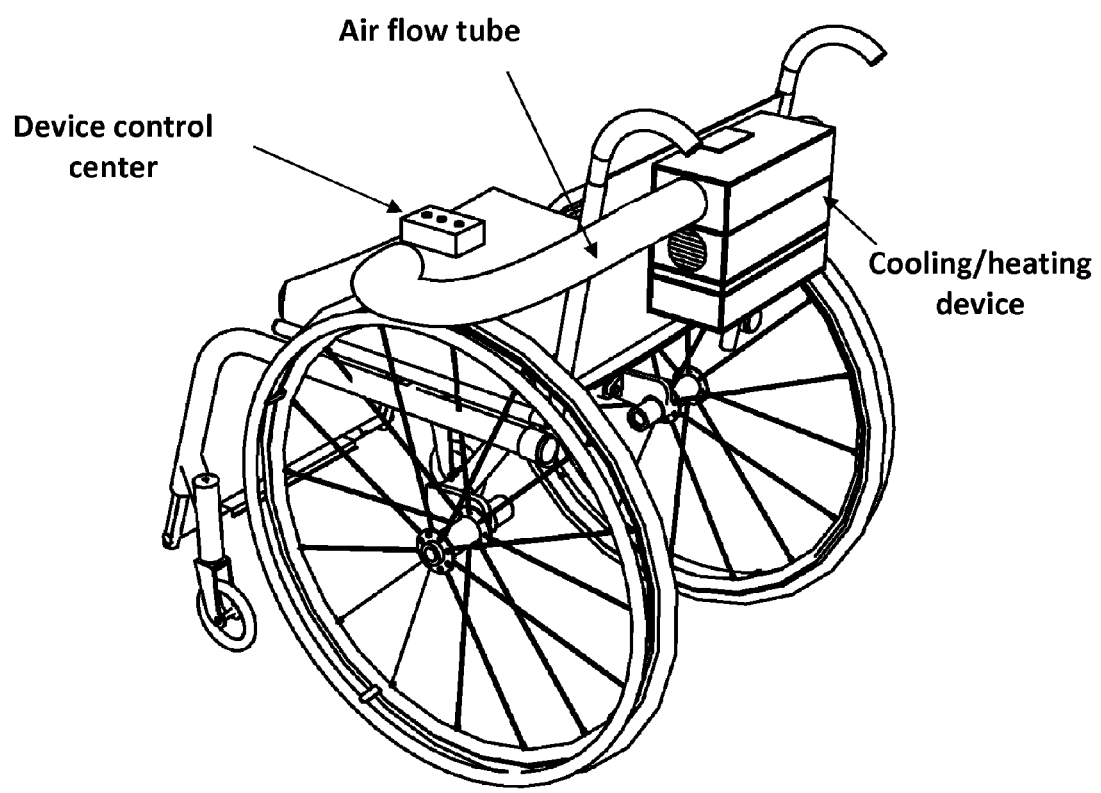
FIG. 6 is a perspective of the second (wheelchair) embodiment of the invention.

FIG. 6 is an illustration of a wheelchair and the implementation of the embodiment of the invention with the thermoregulatory unit 1 positioned at the back of the wheelchair. The control panel 8 is shown away from the thermoregulatory unit 1 to demonstrate the mobility of the control panel.

Figure 7:
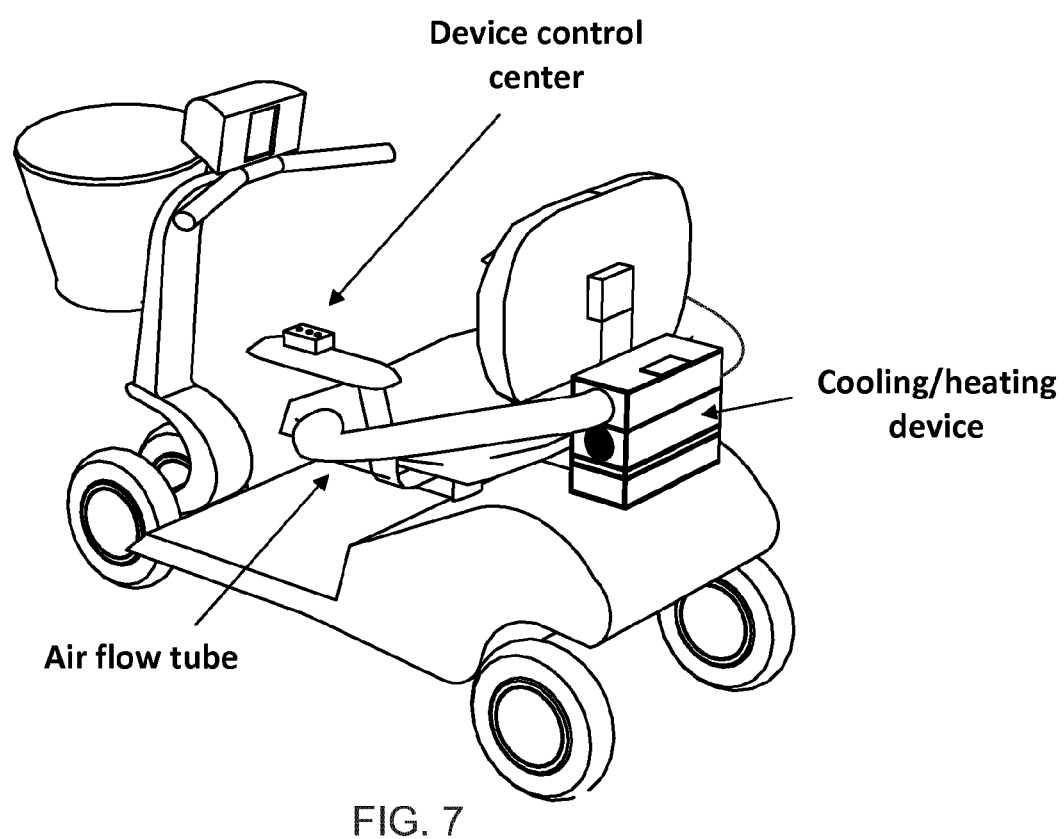
FIG. 7 is a perspective of the third (scooter) embodiment of the invention.

FIG. 7 is an illustration of a scooter and the implementation of the embodiment of the invention with the thermoregulatory unit 1 positioned at the back of the scooter. The tubes going to the user of the scooter need to be insulated and in the illustrations the control panel 8 is away from the thermoregulatory unit 1 to demonstrate the mobility of the control panel.

It will be apparent to those skilled in the art that various modifications and variations can be made to the structure of the present invention without departing from the scope or spirit of the invention. In this view of the foregoing, it is intended that the present invention cover modifications and variations of this invention provided they fall within the scope of the following claims and their equivalents.

What is claimed is:

1. A thermoregulatory unit for a stroller or a wheelchair or a scooter comprising a cover forming an enclosure; said thermoregulatory unit coupled with said enclosure comprising (i) a first chamber to heat or cool the air going into said enclosure and a second chamber to exhaust heat to the ambient;
(ii) said first chamber being next to said second chamber and partitioned with an insulating material;
(iii) at least one thermoelectric or Peltier cooler and heater device installed inside said active first chamber and extends into said second chamber, said thermoelectric device forming a hot or a cold junction by the application of an electric current;
(iv) a heat exchanger means attached to said thermoelectric device to effectively transfer heat from the hot junction of the thermoelectric device to the air inside the first chamber to heat the air or to transfer heat from the air inside the first chamber to the cold junction of said thermoelectric device to cool the air;
(v) said first chamber having an inlet opening, an outlet opening, and a circulating fan to suck the air from the enclosure into the first chamber, heat or cool the air, and then exhaust the air back into the enclosure;
(vi) a set of air tube connecting said inlet and outlet openings of said first chamber to said enclosure forming a recirculating air flow;
(vii) said second chamber having an inlet opening and an outlet opening and a circulating fan to suck the air from the ambient into the second chamber, transfer heat from the second chamber and exhaust the heated or cooled air by the thermoelectric device back into the ambient; and
(viii) an electronics chamber and a battery compartment to power the thermoelectric device and said fans;

whereby said thermoelectric or Peltier cooler and heater device heats the air inside the first chamber when electric current flows in one direction and cools said air when electric current flows in another direction, thereby heating or cooling the enclosure by changing electric current direction.

2. The thermoregulatory unit of claim 1, further comprising directionally adjustable air tubes that provide caregivers the option of directing a portion of heating or cooling that goes into the enclosed compartment toward the caregiver.

3. The thermoregulatory unit of claim 1, further comprising an electronically and/or manually controlled opening to allow ambient air to mix with the recirculating air when required.

4. The thermoregulatory unit of claim 1, wherein said thermoregulatory unit being removable and attachable to plurality of locations on said stroller or wheelchair or scooter.

5. The thermoregulatory unit of claim 1, wherein said thermoregulatory unit being removably attached behind a seat of a stroller or a wheelchair, or a scooter.

6. The thermoregulatory unit of claim 1, further comprising air filters to remove harmful air pollutants and particles.

7. The thermoregulatory unit of claim 1, further comprising a humidifier/dehumidifier.

8. The thermoregulatory unit of claim 1, further comprising thermostatic regulators capable of increasing/decreasing fan speed and/or increasing/decreasing amount of heating/cooling needed based on user inputted preset temperatures.

9. The thermoregulatory unit of claim 1, further comprising a Pulse Width Modulation (PWM) to regulate power and energy requirements to the thermoelectric device.

10. The thermoregulatory unit of claim 1, further comprising attachable and movable control centre for turning various functions of device on/off, including setting compartment temperature, and viewing outside temperature.

* * * * *